(12) United States Patent  (10) Patent No.: US 8,158,799 B2
Schadt et al.  (45) Date of Patent:  Apr. 17, 2012

(54) HYDROXYQUINOLINE DERIVATIVES

(75) Inventors: Oliver Schadt, Rodenbach (DE); Dieter Dorsch, Ober-Ramstadt (DE); Claus Fittschen, Fraenkisch-Crumbach (DE); Matthias Grell, Darmstadt (DE)

(73) Assignee: Merck Patent Gesellschaft MIT Meschraenkter Haftung, Darmstadt (DE)

( * ) Notice: Subject to any disclaimer, the term of this patent is extended or adjusted under 35 U.S.C. 154(b) by 462 days.

(21) Appl. No.: 12/097,153

(22) PCT Filed: Nov. 14, 2006

(86) PCT No.: PCT/EP2006/010902
§ 371 (c)(1),
(2), (4) Date: Jun. 12, 2008

(87) PCT Pub. No.: WO2007/068316
PCT Pub. Date: Jun. 21, 2007

(65) Prior Publication Data
US 2008/0312278 A1  Dec. 18, 2008

(30) Foreign Application Priority Data
Dec. 13, 2005  (DE) .......................... 10 2005 059 479

(51) Int. Cl.
*C07D 401/12* (2006.01)
(52) U.S. Cl. ..................................... 546/171
(58) Field of Classification Search .................. None
See application file for complete search history.

(56) References Cited

U.S. PATENT DOCUMENTS

| | | | |
|---|---|---|---|
| 5,100,759 A | 3/1992 | Sato et al. | |
| 6,030,983 A | 2/2000 | Behforouz et al. | |
| 2004/0029898 A1 | 2/2004 | Boyle et al. | |
| 2005/0107388 A1 | 5/2005 | Brown et al. | |
| 2006/0142333 A1 | 6/2006 | MacDonald et al. | |

FOREIGN PATENT DOCUMENTS

| | | | |
|---|---|---|---|
| JP | 2-187754 A | | 7/1990 |
| JP | 3-103476 A | | 4/1991 |
| JP | 7114158 | * | 5/2005 |
| WO | WO 02/44166 A1 | | 6/2002 |
| WO | WO 03/068749 A1 | | 8/2003 |
| WO | WO 03/080578 A1 | | 10/2003 |

OTHER PUBLICATIONS

Vippagunta et al., Crystalline Solids, 48 Adv. Drug Delivery Rev. 3-26 (2001).*
Madonna et al., Structure-activity Relationship and Mechanism of Action of Antitumor bis 8-Hydroxyquinoline Substituted Benzylamines, 45 Euro. J. Med. Chem., 623-38 (2010).*
Albrecht, M. et al., "Inter- and Intramolecular Hydrogen Bonding in Amide- and Urea-Substituted 8-Hydroxyquinoline Derivatives", XP002412788, Database Caplus [Online] Chemical Abstracts Service. Accession No. 2002:6266 (2002).
Albrecht, M. et al., "Solid-State Structures of Amide-Substituted 8-Hydroxyquinoline Derivatives", XP002412789, Database Caplus [Online] Chemical Abstracts Service. Accession No. 2000:97384 (2000).
Kato, K. et al., "Metal Complexes of Quinolinedione-Aniline Adducts for Optical Recording", XP002412790, Database Caplus [Online] Chemical Abstracts Service. Accession No. 1991:666981 (Apr. 30, 1991).
Watanabe, K. et al., "Infrared-Absorbing-Image-Forming Color Photographic Material", XP002412791, Database Caplus [Online] Chemical Abstracts Service. Accession No. 1991:237515 (Jul. 23, 1990).
Matsumura, K. et al., "Amebicidal 8-Quinolinol Compounds", XP 002412792, Database Caplus [Online] Chemical Abstracts Service. Accession No. 1961:8120 (1960).
Matsumura, K. et al., "Synthesis of Quinoline Derivatives. VI. Preparation of Certain Acylamino Derivatives of 8-Hydroxyquinoline", XP002412793, Database Caplus [Online] Chemical Abstracts Service. Accession No. 1931:8710 (1931).
Kato, K. et al. "Metal-Containing Indoaniline Based Compound", English Abstract of Japanese Patent Publication No. JP03103476 A2, Published: Apr. 30, 1991, Application No. JP1989000241385, filed Sep. 18, 1989 (Delphion).
Kato, K. et al "Metal-Containing Indoaniline Based Compound", English Abstract of Japanese Patent Publication No. JP03103476 A2, Published: Apr. 30, 1991, Application No. JP1989000241385, filed Sep. 18, 1989 (Patent Abstracts of Japan).
Watanabe, K. et al. "Color Photosensitive Material", English Abstract of Japanese Patent Publication No. JP02187754, Published: Jul. 23, 1990, Application No. JP1989000008153, filed Jan. 17, 1989 (Delphion).
Watanabe, K. et al. "Color Photosensitive Material", English Abstract of Japanese Patent Publication No. JP02187754, Published: Jul. 23, 1990, Application No. JP1989000008153, filed Jan. 17, 1989 (Patent Abstracts of Japan).

(Continued)

*Primary Examiner* — Janet Andres
*Assistant Examiner* — Timothy R Rozof
(74) *Attorney, Agent, or Firm* — Millen, White, Zelano & Branigan, P.C.

(57) ABSTRACT

Compounds of the formula I in which X, Y, $R^1$, $R^{1'}$, $R^2$, $R^3$ have the meanings indicated in Claim 1, are inhibitors of cell proliferation and can be employed for the treatment of tumors.

(I)

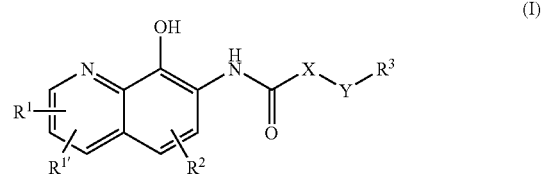

16 Claims, No Drawings

OTHER PUBLICATIONS

International Search Report completed Dec. 22, 2006 in International Application No. PCT/EP2006/010902. International filing date: Nov. 14, 2006. International Publication No. WO 2007/068316, Published Jun. 21, 2007.

M. Albrecht et al., "Inter- and Intramolecular Hydrogen Bonding in Amide- and Urea-Substituted 8-Hydroxyquinoline Derivatives", XP002412788, Database Caplus [Online] Chemical Abstracts Service, (2002).

M. Albrecht et al., "Solid-State Structures of Amide-Substituted 8-Hydroxyquinoline Derivatives", XP002412789, Database Caplus [Online] Chemical Abstracts Service, (2000).

K. Katsunori et al., "Metal Complexes of Quinolinedione-Aniline Adducts for Optical Recording", XP002412790, Database Caplus [Online] Chemical Abstracts Service, (1991).

K. Watanabe et al., "Infrared-Absorbing-Image-Forming Color Photographic Material", XP002412791, Database Caplus [Online] Chemical Abstracts Service, (1991).

K. Matsumura et al "Amebicidal 8-Quinolinol Compounds", XP 002412792, Database Caplus [Online] Chemical Abstracts Service, (1961).

K. Matsumura et al., "Synthesis of Quinoline Derivatives. VI. Preparation of Certain Acylamino Derivatives of 8-Hydroxyquinoline", XP002412793, Database Caplus [Online] Chemical Abstracts Service, (1931).

* cited by examiner

HYDROXYQUINOLINE DERIVATIVES

The invention relates to compounds of the formula I

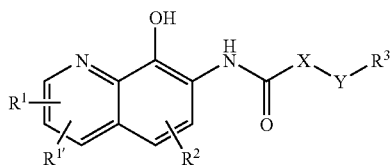

in which
R$^1$, R$^{1'}$, R$^2$ each, independently of one another, denote H, OH, OA, SH, SA, SOA, SO$_2$A, Hal, NO$_2$, NH$_2$, NHA, NAA', A, SO$_2$NH$_2$, SO$_2$NHA, SO$_2$NAA', CONH$_2$, CONHA, CONAA', NACOA', NASO$_2$A', COOH, COOA or CN,
R$^3$ denotes A, Ar, Het, NR$^4$R$^5$ or CHR$^4$R$^5$,
  where at least one of the radicals
  R$^4$ or R$^5$ denotes (CH$_2$)$_n$Ar or (CH$_2$)$_n$Het,
R$^4$, R$^5$ each, independently of one another, denote H, A, (CH$_2$)$_n$Ar or (CH$_2$)$_n$Het,
X is absent, denotes CH$_2$, NR$^6$ or O,
Y is absent or denotes alkylene having 1-3 C atoms,
R$^6$ denotes H or A,
A, A' each, independently of one another, denote unbranched or branched alkyl having 1-10 C atoms,
  in which 1-7H atoms may be replaced by F, Cl and/or Br,
  cycloalkyl having 3-8 C atoms or
  cycloalkylalkylene having 4-10 C atoms,
Hal denotes F, Cl, Br or I,
Ar denotes a saturated, unsaturated or aromatic carbocycle having 5-14 C atoms which is unsubstituted or mono-, di- or trisubstituted by OH, OA, SH, SA, SOA, SO$_2$A, Hal, NO$_2$, NH$_2$, NHA, NAA', A, SO$_2$NH$_2$, SO$_2$NHA, SO$_2$NAA', CONH$_2$, CONHA, CONAA', NACOA', NASO$_2$A', COOH, COOA, COA, CHO or CN,
Het denotes a mono-, bi- or tricyclic saturated, unsaturated or aromatic heterocycle having 1 to 4 N, O and/or S atoms, which may be unsubstituted or mono-, di- or trisubstituted by OH, OA, SH, SA, SOA, SO$_2$A, Hal, NO$_2$, NH$_2$, NHA, NAA', A, SO$_2$NH$_2$, SO$_2$NHA, SO$_2$NAA', CONH$_2$, CONHA, CONAA', NACOA', NASO$_2$A', COOH, COOA, CHO, COA, CN, =S, =NH, =NA and/or =O (carbonyl oxygen),
n denotes 0, 1 or 2,
and pharmaceutically usable derivatives, solvates, salts, tautomers and stereoisomers thereof, including mixtures thereof in all ratios.

The invention was based on the object of finding novel compounds having valuable properties, in particular those which can be used for the preparation of medicaments.

It has been found that the compounds of the formula I and salts and/or solvates thereof have very valuable pharmacological properties while being well tolerated.

In particular, they exhibit a cell proliferation-inhibiting action as antagonists or agonists. The compounds according to the invention can therefore be used for the control and/or treatment of tumours, tumour growth and/or tumour metastases.

The antiproliferative action can be tested in an HCT116 proliferation assay.

Other quinoline derivatives for combating cancer are known, for example, from U.S. Pat. No. 6,030,983, from U.S. Pat. No. 5,712,289, from U.S. Pat. No. 5,646,150 or WO 94/29308.

Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore useful in the treatment of immune deficiency induced by HIV-1 (Human Immunodeficiency Virus Type 1).

Cancer-like hyperproliferative diseases to be are regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. solvates are, for example, mono- or dihydrates or alkoxides.

The term pharmaceutically usable derivatives is taken to mean, for exampie, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to claims 1-13 and pharmaceutically usable derivatives, salts, solvates and stereoisomers thereof, characterised in that a) for the preparation of compounds of the formula I in which X is absent or denotes $CH_2$,
a compound of the formula II

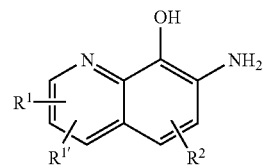

in which $R^1$, $R^{1'}$ and $R^2$ have the meanings indicated in claim 1,
is reacted with a compound of the formula III

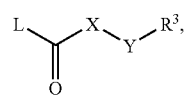

in which X is absent or denotes $CH_2$,
Y and $R^3$ have the meanings indicated in claim 1,
and L denotes Cl, Br, I or a free or reactively functionally modified OH group,
or
b) for the preparation of compounds of the formula I in which X denotes $NR^6$,
a compound of the formula II is reacted with a compound of the formula IV

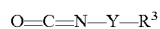

in which
Y and $R^3$ have the meanings indicated in claim 1,
or
c) in that they are liberated from one of their functional derivatives by treatment with a solvolysing or hydrogenolysing agent,
or
d) for the preparation of compounds of the formula I in which X denotes $NR^6$ or O,
a compound of the formula V

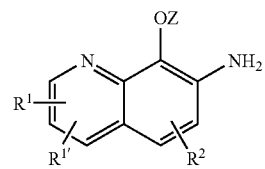

in which $R^1$, $R^{1'}$ and $R^2$ have the meanings indicated in claim 1,
and Z denotes a hydroxyl-protecting group,
is reacted with a coupling reagent selected from the group
a) isopropylidene chloroformate,
b) p-nitrophenyl chloroformate,
c) diphosgene,
d) triphosgene,
and a compound of the formula VI

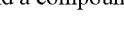

in which X denotes $NR^6$ or O,

Y and R³ have the meanings indicated in claim 1,
and the hydroxyl-protecting group Z is subsequently cleaved off,
and/or
a base or acid of the formula I is converted into one of its salts.

Above and below, the radicals X, Y, R¹, R¹', R² and R³ have the meanings indicated for the formula I, unless expressly stated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl preferably denotes cyclopropyl, cyclobutyl, cyclopentyl, cyclohexyl or cycloheptyl.

Cycloalkylalkylene preferably denotes cyclopropylmethyl, cyclobutylmethyl, cylopentylmethyl, cyclohexylmethyl or cycloheptylmethyl.

Alkylene is preferably unbranched and preferably denotes methylene, ethylene or propylene.

A saturated, unsaturated or aromatic carbocycle having 5-14 C atoms preferably denotes cyclopentyl, cyclohexyl, cycloheptyl, phenyl, naphthyl, biphenyl or tetrahydronaphthyl.

Ar preferably denotes a saturated, unsaturated or aromatic carbocycle having 6-14 C atoms which is unsubstituted or mono-, di- or trisubstituted by OH, OA, Hal and/or A.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl,
further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3, 5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

Ar particularly preferably denotes phenyl, naphthyl or 1,2, 3,4-tetrahydronaphthalene, each of which is unsubstituted or mono-, di- or trisubstituted by OH, OA, Hal and/or A.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Unsubstituted Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het preferably denotes a monocyclic aromatic heterocycle having 1 to 3 N, O and/or S atoms. Het very particularly preferably denotes pyridyl, pyrimidinyl, thienyl or furyl.

R¹, R¹' preferably denote H.

R² preferably denotes H, OA or Hal.

X is preferably absent or denotes CH₂ or NH.

Y is preferably absent.

R³ preferably denotes

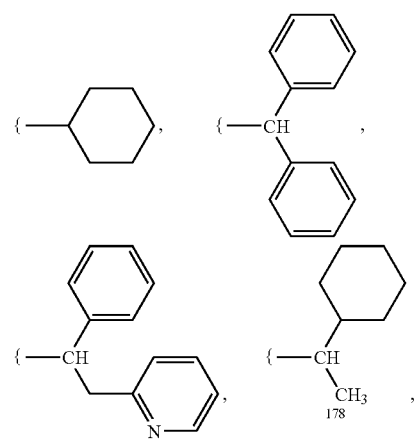

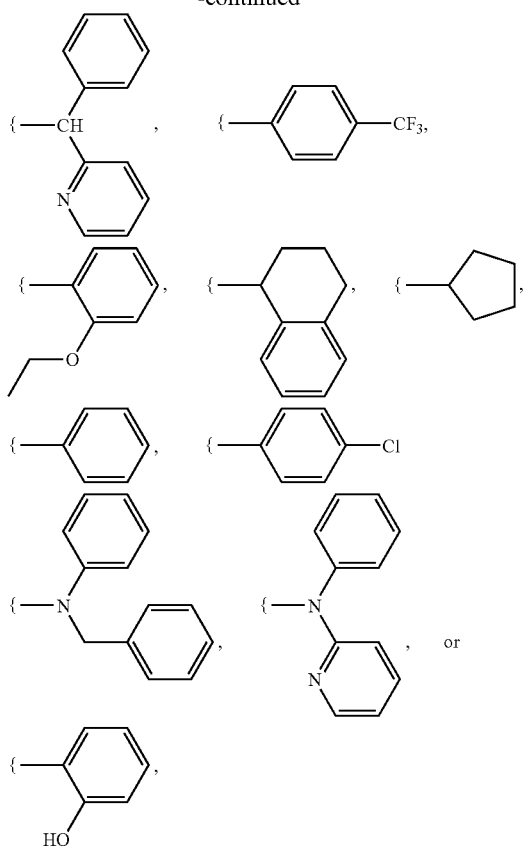

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ik, which conform to the formula I and in which the radicals not designated in greater detail have the meaning indicated for the formula I, but in which in Ia $R^1$, $R^{1'}$ denotes H;

in Ib $R^2$ denotes H, OA or Hal;

in Ic Ar denotes a saturated, unsaturated or aromatic carbocycle having 5-14 C atoms which is unsubstituted or mono-, di- or trisubstituted by OH, OA, Hal and/or A;

in Id Het denotes a monocyclic aromatic heterocycle having 1 to 3 N, O and/or S atoms;

in Ie X is absent, denotes $CH_2$ or NH;

in If Y is absent;

in Ig Ar denotes phenyl, naphthyl or 1,2,3,4-tetrahydronaphthalene, each of which is unsubstituted or mono-, di- or trisubstituted by OH, OA, Hal and/or A;

in Ih Het denotes pyridyl, pyrimidinyl, thienyl or furyl;

in Ii $R^3$ denotes

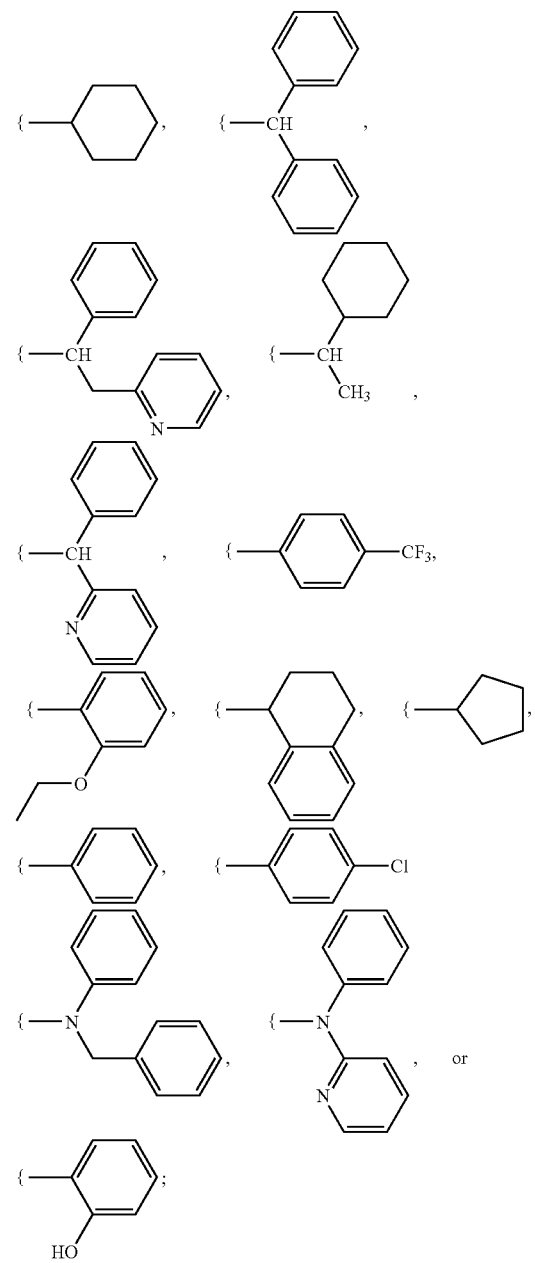

in Ij
$R^1$, $R^{1'}$ denote H,
$R^2$ denotes H, OA or Hal,
$R^3$ denotes A, Ar, Het, $NR^4R^5$ or $CHR^4R^5$,
  where at least one of the radicals
  $R^4$ or $R^5$ denotes $(CH_2)_n Ar$ or $(CH_2)_n Het$,
$R^4$, $R^5$ each, independently of one another, denote H, A, $(CH_2)_n Ar$ or $(CH_2)_n Het$,
X is absent, denotes $CH_2$ or NH,
Y is absent,
Ar denotes a saturated, unsaturated or aromatic carbocycle having 5-14 C atoms which is unsubstituted or mono-, di- or trisubstituted by OH, OA, Hal and/or A,
Het denotes a monocyclic aromatic heterocycle having 1 to 3 N, O and/or S atom, A in each case, independently of one another, denotes unbranched or branched alkyl having 1-10 C atoms,
in which 1-7H atoms may be replaced by F, Cl and/or Br,
cycloalkyl having 3-8 C atoms or
cycloalkylalkylene having 4-10 C atoms,
Hal denotes F, Cl, Br or I,
n denotes 0, 1 or 2;
in Ik $R^1$, $R^{1'}$ denote H,
$R^2$ denotes H, OA or Hal,
$R^3$ denotes A, Ar, Het, $NR^4R^5$ or $CHR^4R^5$,
where at least one of the radicals
$R^4$ or $R^5$ denotes $(CH_2)_nAr$ or $(CH_2)_nHet$,
$R^4$, $R^5$ each, independently of one another, denote H, A, $(CH_2)_nAr$ or $(CH_2)_nHet$,
X is absent, denotes $CH_2$ or NH,
Y is absent,
Ar denotes phenyl, naphthyl or 1,2,3,4-tetrahydronaphthalene, each of which is unsubstituted or mono-, di- or tri-substituted by OH, OA, Hal and/or A,
Het denotes pyridyl, pyrimidinyl, thienyl or furyl,
A in each case, independently of one another, denotes unbranched or branched alkyl having 1-10 C atoms,
in which 1-7H atoms may be replaced by F, Cl and/or Br,
cycloalkyl having 3-8 C atoms or
cycloalkylalkylene having 4-10 C atoms,
Hal denotes F, Cl, Br or I,
n denotes 0, 1 or 2;
and pharmaceutically usable derivatives, salts, solvates, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting compounds of the formula II and with compounds of the formula III.

The compounds of the formula II and of the formula III are generally known. If they are novel, however, they can be prepared by methods known per se.

The reaction is carried out in the presence of a carbodiimide, such as, for example, EDCI (N-ethyl-N,N'-(dimethylaminopropyl)carbodiimide) or dicyclohexylcarbodiimide, optionally in the presence of an organic base, such as, for example, N-methylmorpholine, and in an inert solvent.

An activated ester can advantageously also be formed in situ, for example through addition of HOBt (hydroxybenzotriazole) or N-hydroxysuccinimide. In the compounds of the formula III, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Depending on the conditions used, the reaction time is between a few minutes and 14 days, the reaction temperature is between about −15° and 150°, normally between −5° and 90°, particularly preferably between 20° and 60° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to THF, dichloromethane and/or DMF.

Compounds of the formula I can furthermore be obtained by reacting compounds of the formula II with compounds of the formula IV.

The compounds of the formula IV are generally known. If they are novel, however, they can be prepared by methods known per se.

The reaction is generally carried out in an inert solvent, in the presence of an organic base, such as triethylamine, dimethylaniline, pyridine or quinoline. Depending on the conditions used, the reaction time is between a few minutes and 14 days, the reaction temperature is between about 0° and 150°, normally between 15° and 90°, particularly preferably between 15° and 30° C. Suitable inert solvents are those mentioned above.

The cleavage of an ether is carried by methods as are known to the person skilled in the art.

A standard method of ether cleavage, for example of a methyl ether, is the use of boron tribromide.

Hydrogenolytically removable groups, for example the cleavage of a benzyl ether, can be cleaved off, for example, by treatment with hydrogen in the presence of a catalyst (for example a noble-metal catalyst, such as palladium, advantageously on a support, such as carbon). Suitable solvents here are those indicated above, in particular for example alcohols, such as methanol or ethanol, or amides, such as DMF. The hydrogenolysis is generally carried out at temperatures between about 0 and 100° and pressures between about 1 and 200 bar, preferably at 20-300 and 1-10 bar.

Ester can be saponified, for example, using acetic acid or using NaOH or KOH in water, water/THF or water/dioxane, at temperatures between 0 and 100°.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' is an amino-protecting group, for example BOC or CBZ) instead of an $NH_2$ group.

Preference is furthermore given to starting materials which carry a hydroxyl-protecting group instead of the H atom of a hydroxyl group, for example those which conform to the formula I, but contain an R"O-phenyl group (in which R" is a hydroxyl-protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5 N HCl in dioxane at 15-300, and the FMOC group can be cleaved off using an approximately 5 to 50% solution of dimethylamine, diethylamine or piperidine in DMF at 15-30°.

The trityl group is employed to protect the amino acids histidine, asparagine, glutamine and cysteine. They are cleaved off, depending on the desired end product, using TFA/10% thiophenol, with the trityl group being cleaved off from all the said amino acids; on use of TFA/anisole or TFA/thioanisole, only the trityl group of H is, Asn and Gln is cleaved off, whereas it remains on the Cys side chain.

The Pbf (pentamethylbenzofuranyl) group is employed to protect Arg. It is cleaved off using, for example, TFA in dichloromethane.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100 and pressures between about 1 and 200 bar, preferably at 20-300 and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Compounds of the formula I in which X denotes $NR^6$ or O can preferably be obtained by reacting a compound of the formula V with a coupling reagent selected from the group
  a) isopropylidene chloroformate,
  b) p-nitrophenyl chloroformate,
  c) diphosgene,
  d) triphosgene,
and a compound of the formula VI. The reaction is preferably carried out as a one-pot reaction.

The reaction is generally carried out in an inert solvent.

Depending on the conditions used, the reaction time is between a few minutes and 14 days, the reaction temperature is between about −15° and 150°, normally between −5° and 90°, particularly preferably between 20° and 60° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to THF, dichloromethane, pyridine and/or DMF.

The reaction is generally carried out in the presence of an acid-binding agent, preferably an organic base, such as DIPEA, triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

The protecting group is subsequently cleaved off, as indicated above.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylam idophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions pre-pared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment and control of cancer diseases.

The present invention encompasses the use of the compounds of the formula I and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds of the formula I and/or physiologically acceptable salts and solvates thereof for the preparation of a medicament for the treatment or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease where the disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)Platinum, benzylguanine, glufosfamide, GPX100, (trans,trans,trans)bis-mu-(hexane-1,6-diamine)-mu-[diamine-Platinum(II)]bis[diamine(chloro)Platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]-acridin-6-one, N-[1-[2(diethylamino)ethylamino]-7-methoxy-9-oxo-9H-thio-xanthen-4-ylmethyl]formamide, N-(2-(dimethylamino)ethyl)acridine- 4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo-(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal anti-bodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Evidence of the Action of Pharmacological Inhibitors on the Proliferation of Tumour Cells In Vitro 1.0 Background The present experimental description describes the inhibition of tumour cell proliferation by active ingredients.

The cell proliferation is estimated by measurement of the uptake of propidium iodide. In the dissolved, free state, propidium iodide is colourless and does not fluoresce. It is prevented from entering healthy cells. However, if cells have been killed by addition of the detergent NP40, cell membrane and nuclear membrane become permeable. PI attaches itself to the DNA of the cell nuclei and fluoresces in this complex. This fluorescence is measured in the fluorimeter.

2.0 Experimental Procedure 2.1 Cell Culture commercially available colon carcinoma cell lines 2.1.1 Detachment of Cells Growing in an Adherent Manner (Passage)

2.1.2 Determination of Cell Number and Vitality 2.2 Seeding of the Cells for the Experiment 10,000 cells are plated out per well, in a volume of 180 µl, in a 96-hole plate. The outer rows A1-12, 1A-H, 12A-H and H1-12 are only filled with 200 µl of medium or buffer.

2.2.1 Pre-Incubation of the Cells

The cells are incubated for 24 hours, at 37° C. and 10% $CO_2$ gassing.

2.3 Plate Scheme and Addition of Substances:

In order to test active substances, the corresponding dilutions must first be produced and assigned to the wells. The scheme of a 1:3 dilution indicated here as an example can be varied correspondingly as desired. The scheme described is designed for 4 test substances.

The arrangement is only a suggestion. Depending on the objective, another division can also be selected.

|   | EMD 1 | | EMD 2 | | EMD 3 | | EMD 4 | | Controls | | |
|---|---|---|---|---|---|---|---|---|---|---|---|
| 1 | 2 | 3 | 4 | 5 | 6 | 7 | 8 | 9 | 10 | 11 | 12 |
| A | | | | | | | | | | | |
| B | | | | | | | | | Control 100% value | | |
| C | | | | | | | | | | | |
| D | | | | | | | | | DMSO solvent control | | |
| E | | | | | | | | | | | |
| F | | | | | | | | | Pos. control | | |
| G | | | | | | | | | | | |
| H | | | | | | | | | | | |

100% Values, Solvent Control or Positive Control (Column B-G, Wells 10+11):

20 µl of medium, solvent dilution or the corresponding dilution of the positive control (IC50) are pipetted into these holes.

Substance groups (column B-G, wells 2-9): 20 µl of substance dilution are pipetted into these holes.

Substance dilution series in extra plate (example for 1:3 dilution):

147 µl of medium is introduced into each of the wells of row B of the extra plate in columns 1, 2, 3, 4, and 3 µl of the test substance are added (=300 µM). 100 µl of medium are introduced into rows C-G, columns 1-4. 50 µl are then transferred into row C using a multichannel pipette, mixed 8×, and 50 µl are then transferred from this row into row D. This is continued correspondingly until row G has been reached, in which, after mixing, 50 µl of the dilution are removed and discarded. 100 µl of each desired dilution are now located in the extra plate, and it is now only necessary to transfer 20 µl directly into the test plate.

| | | EMDs: 15 mM DMSO | | |
|---|---|---|---|---|
| | | Total volume/well [µl]: 200.0 | | |
| | Test concentration/well | Vol. dil. [µl] 20 Concentrate | Dil. factor 1: | For plate dilution Min. vol./well [µl] 100 150 µl from 1) |
| 1) | 30.0000 µM | 300.0000 µM ----> | 50 | Stock soln. 3.0 µl + 147 µl of medium |
| 2) | 10.0000 µM | 100.0000 µM ----> | 3 | 50 µl from 1) + 100 µl of medium |
| 3) | 3.3333 µM | 33.3333 µM ----> | 3 | 50 µl from 2) + 100 µl of medium |
| 4) | 1.1111 µM | 11.1111 µM ----> | 3 | 50 µl from 3) + 100 µl of medium |

-continued

EMDs: 15 mM DMSO
Total volume/well [µl]: 200.0

| Test concentration/well | Vol. dil. [µl] 20 Concentrate | Dil. factor 1: | For plate dilution Min. vol./well [µl] 100 150 µl from 1) |
|---|---|---|---|
| 5) 0.3704 µM | 3.7037 µM ----> | 3 | 50 µl from 4) + 100 µl of medium |
| 6) 0.1235 µM | 1.2346 µM ----> | 3 | 50 µl from 5) + 100 µl of medium |
| 7) 0 µM | 0 µM | | |

2.4 Incubation of the Cells

The plate is incubated at 37° C. and 10% CO2 gassing for 3 days.

The cells multiplying in this time are determined by means of propidium iodide.

2.5 Measurement of Cell Proliferation by Means of Propidium Iodide 2.5.1 Addition of PI and NP40

20 µl of PI stock solution and 10 µl of NP40 stock solution are required per well. Since each plate has 72 wells charged with PI and with NP40, 1440 µl of the PI stock solution and 720 µl of the NP40 stock solution are required per plate. Taking into account pipetting losses, 1.8 ml of PI stock solution are thus taken and mixed with 0.9 ml of the NP40 stock solution immediately before pipetting in. 30 µl of the PI/NP40 mixture are now pipetted into each of the wells of the plate, each of which contain 200 µl of medium. The plate is subsequently placed in the incubator for 2 hours.

2.5.2 Measurement and Calculation

The plate(s) is measured in a fluorescence photometer at a wavelength Ex. 520 nm and Em of 620 nm. The background (=medium+PI) is subtracted from all values, which are subsequently averaged (double values) and expressed or calculated in % of control.

$$\text{Calculation:} \frac{100 * (\text{average of the individual values} - \text{average of background})}{(\text{average of the 100\% individual values} - \text{average of background})}$$

An $IC_{50}$ (half-maximum action) can now be calculated using a statistics program such as, for example, RS1.

$IC_{50}$ data for some compounds according to the invention are indicated in Table 1.

3.0 Materials, Reagents and Solutions 3.1

| Materials | Company/Cat.No. |
|---|---|
| Ascent Fluoroskan | Labsystems S No.: 374 009-751 |
| 8-channel pipette (e.g. Finnpipette, 5-50 µl) | Kühn u. Bayer 4142407 |
| 8-channel pipette (e.g. Finnpipette, 50-300 µl) | Kühn u. Bayer 4142417 |
| 12-channel pipette (e.g. Finnpipette, 5-50 µl) | Kühn u. Bayer 4172307 |
| 12-channel pipette (e.g. Finnpipette, 50-300 µl) | Kühn u. Bayer 4172317 |
| Multipette 4780 | Eppendorf 4780 |
| Varipette 200-1000 µl | Eppendorf 4810 |
| Varipette 10-100 µl | Eppendorf 4810 |
| Varipette 0.5-10 µl | Eppendorf 4810 |
| Sterile syringes, standard tips 10 µl | Eppendorf 22195 |
| Sterile syringes, standard tips 1000 µl | Eppendorf 35443 |
| Sterile syringes, BR-38 100 µl | Bio-Rad 223-9038 |
| Polypropylene tubes, 50 ml, sterile | Falcon 2070 |
| Polypropylene tubes, 6 ml, sterile | Falcon 2063 |
| Polypropylene tubes, 14 ml, sterile | Falcon 2059 |
| 96-well microtitre plate for tissue culture, sterile | Nunc 167008 |
| Reagent reservoir, sterile | Costar 4870 |
| Reaction vessels, 1.5 ml polypropylene | Eppendorf 3810 |
| Sterile filters (bottle top filters) 0.22 µm | Falcon 7105 |

3.2

| Reagents and stock solutions Culture medium: | Company/Cat. No. |
|---|---|
| MEM ALPHA MEDIUM Storage at +4° C. | Gibco 22571-020 |
| Foetal calf serum (FCS), sterile Portioned: 50 ml in 50 ml polypropylene tubes Storage at −20° C. | Gibco 011-06290 M |
| Penicillin/streptomycin Storage at −20° C. | Gibco 15140-114 |
| L-glutamine (200 mM) Storage at −20° C. | Gibco 25030-024 |
| Nonidet ® P40 [Nonylphenyl polyethylene glycol] | Bio Chemika 74385 |
| Propidium iodide | Sigma P4170 |
| DMSO (dimethyl sulfoxide) for spectroscopy | Merck 2950 |

3.3 Preparation of Solutions 3.3.1 Culture Medium:

500 ml (1 bottle) of alpha-MEM

+50 ml of FCS=10%

+5 ml of penicillin/streptomycin

+5 ml of glutamine=2 mM

Storage at +4° C.

3.3.2 Test Substances:

Prepare the desired stock solution at 15 µM in DMSO. Adjust to ten times the concentration to be tested in the cell culture (see above) by dilution in culture medium.

3.3.3 Propidium Iodide Stock Solution

Dissolve 20 mg of PI in 20 ml of PBS and store tube at 4° C. with light protection (wrap in aluminium foil).

3.3.4 NP40 Stock Solution

11% dissolved in water and store at 4° C.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS):

EI (electron impact ionisation) $M^+$

FAB (fast atom bombardment) $(M+H)^+$

ESI (electrospray ionisation) $(M+H)^+$

APCI-MS (atmospheric pressure chemical ionisation-mass spectrometry) $(M+H)^+$.

HPLC Gradient System

Column:

ChromolithPerformance RP-18e (Merck KGaA, Cat. 1.02129.0001)

Eluents:

Eluent A: 0.1 M aqueous NaH2PO4

Eluent B: acetonitrile+10% of water

Flow rate: 4 ml/min

Gradient:

0 min 1% of B 1 min 1% of B 7 min 99% of B 8 min 99% of B

EXAMPLE 1

The preparation of N-(5-chloro-8-hydroxyquinolin-7-yl)-3,3-diphenylpropionamide ("A1") is carried out analogously to the following scheme

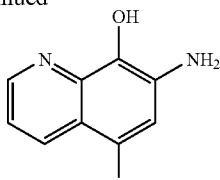

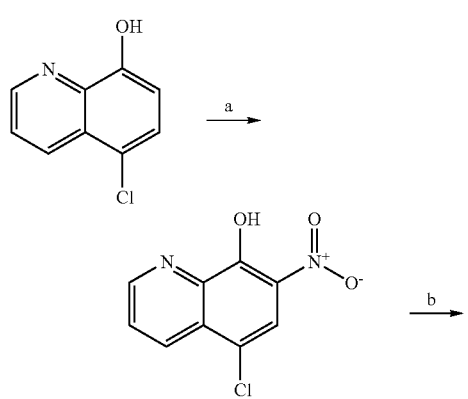

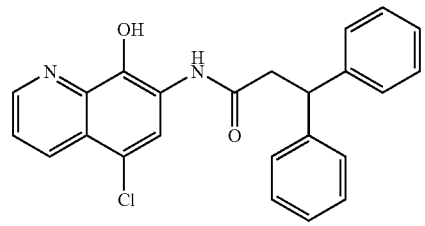

a) 10 g of 5-chloroquinolin-8-ol are dissolved in 56 ml of conc. $H_2SO_4$, a mixture of 100% of 2.8 ml of $HNO_3$+0.5 ml of $H_2O$ is added dropwise with cooling and stirring at max. 0° C., and the mixture is subsequently stirred for a further 2 h without cooling.

Work-up: The mixture is stirred into 300 ml of ice/$H_2O$, the resultant precipitate is separated off, washed a number of times with $H_2O$, stirred in a little cold MeOH, filtered off with suction and washed with ether, giving 10.2 g of 5-chloro-7-nitroquinolin-8-ol (81%), m.p. 201-202°; HPLC: RT 5.36 min.

b) 10.135 g of 5-chloro-7-nitroquinolin-8-ol in are suspended in a mixture of 150 ml of MeOH and 150 ml of $H_2O$ in an $N_2$-flushed 500 ml three-necked flask, 40.54 g of sodium dithionite are added in portions with stirring, and the mixture is stirred at RT for a further 16 h, during which the suspension changes colour from intense orange to pale yellow.

The product is filtered off with suction, washed with copious $H_2O$ and dried at 70° C.

Yield: 8.16 g (93%) of 5-chloro-7-aminoquinolin-8-ol, m.p. 165-166°;

HPLC: RT 4.77 min.

c) 1.131 g of 3,3-diphenylpropionic acid is initially introduced in 10 ml of abs. THF in a 100 ml one-necked flask, 0.892 g of 1,1'-carbonyldiimidazole is added, the mixture is stirred at RT for 2 h, then 0.973 g of 5-chloro-7-aminoquinolin-8-ol is added, and the mixture is stirred under reflux for 20 h.

The mixture is diluted with 50 ml of $H_2O$, stirred vigorously for 10 min, the resultant precipitate is filtered off with suction, washed with a little MeOH and chromatographed over 50 g of silica gel, giving 1.155 g (57%) of "A1", m.p. 206-207°;

$^1$H NMR (250 MHz, DMSO-$d_6$) δ 10.451 (SB, 1H), 9.710 (S, 1H). 8.930 (D, 1H), 8.426 (D, 1H), 8.243 (S, 1H), 7.631 (Q, 1H), 7.375 (M, 4H), 7.292 (M, 4H), 7.170 (T, 2H), 4.604 (T, 1H), 3.335 (D, 2H).

The following compounds are obtained analogously

| Compound No. | Structure/name | Analytical data |
|---|---|---|
| "A2" | 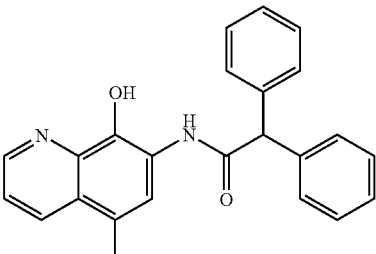<br>N-(5-chloro-8-hydroxyquinolin-7-yl)-2,2-diphenyl-acetamide | M.p. 217-218°<br>$^1$H NMR (250 MHz, DMSO-$d_6$) δ 10.62 (S, 1H), 10.045 (S, 1H), 8.934 (DD, 1H), 8.452 (M, 2H), 7.646 (Q, 1H), 7.331 (M, 10H), 5.647 (S, 1H) |
| "A3" | 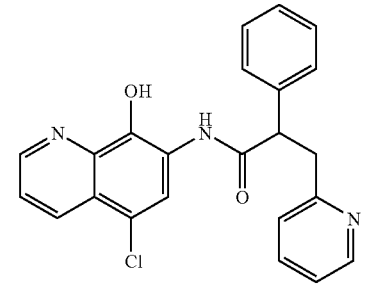<br>N-(5-chloro-8-hydroxyquinolin-7-yl)-2-phenyl-3-pyridin-2-ylpropionamide | M.p. 219-220°<br>$^1$H NMR (250 MHz, DMSO-$d_6$) δ 10.505 (SB, 1H), 9.796 (S, 1H), 8.911 (D, 1H), 8.430 (M, 2H), 8.351 (M, 2H), 7.631 (M, 2H), 7.491 (D, 2H), 7.331 (T, 2H), 7.255 (M, 2H), 4.526 (T, 1H), 3.413 (DD, 1H), 3.053 (DD, 1H) |
| "A4" | 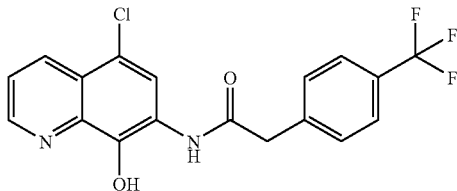<br>N-(5-chloro-8-hydroxyquinolin-7-yl)-2-(4-trifluoromethylphenyl)acetamide | |
| "A5" | 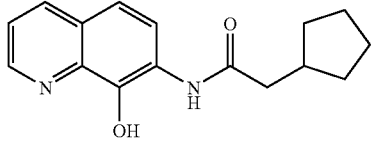<br>2-Cyclopentyl-N-(8-hydroxyquinolin-7-yl)-acetamide | |
| "A6" | 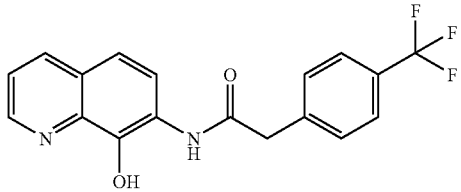<br>N-(8-hydroxyquinolin-7-yl)-2-(4-trifluoromethyl-phenyl)acetamide | |

-continued

| Compound No. | Structure/name | Analytical data |
|---|---|---|
| "A7" | 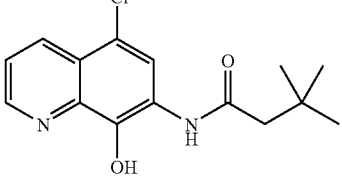<br>N-(5-chloro-8-hydroxyquinolin-7-yl)-3,3-dimethyl-butyramide | |
| "A8" | 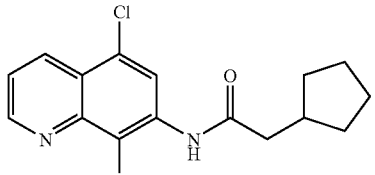<br>N-(5-chloro-8-hydroxyquinolin-7-yl)-2-cyclopentylacetamide | |
| "A9" | 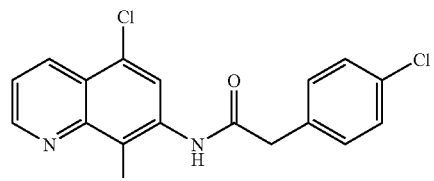<br>N-(5-chloro-8-hydroxyquinolin-7-yl)-2-(4-chloro-phenyl)acetamide | |
| "A10" | 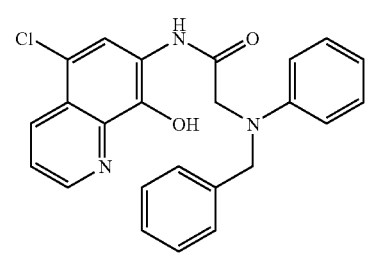<br>2-(Benzylphenylamino)-N-(5-chloro-8-hydroxy-quinolin-7-yl)acetamide | |
| "A11" | 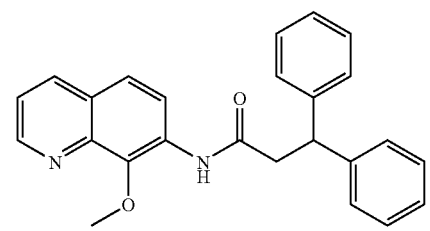<br>N-(8-methoxyquinolin-7-yl)-3,3-diphenylpropion-amide | |
| "A12" | 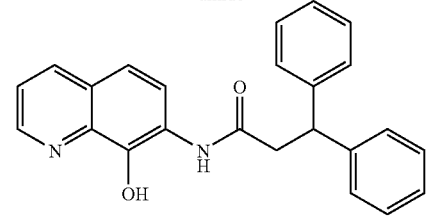<br>N-(8-hydroxyquinolin-7-yl)-3,3-diphenylpropion-amide<br>[from "A11" by ether cleavage using BI$_3$] | |

| Compound No. | Structure/name | Analytical data |
|---|---|---|
| "A13" | 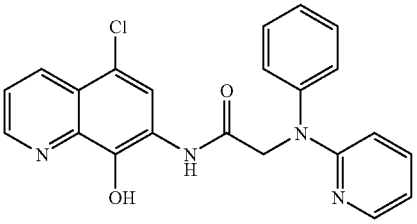<br>N-(5-chloro-8-hydroxyquinolin-7-yl)-2-(phenyl-pyridin-2-ylamino)acetamide | |

EXAMPLE 2

The preparation of 1-(5-chloro-8-hydroxyquinolin-7-yl)-3-(phenylpyridin-2-ylmethyl)urea ("A14") is carried out analogously to the following scheme

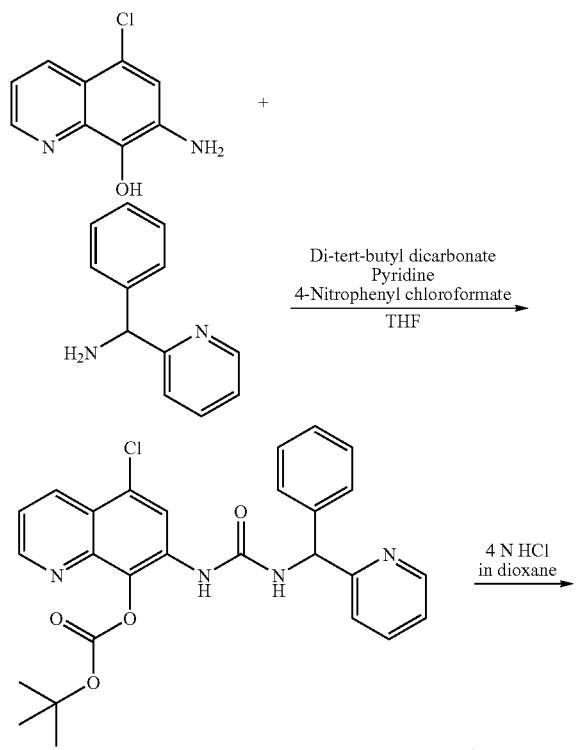

dihydrochloride
"A14"

2.1 a) 480 mg (2.20 mmol) of di-tert-butyl dicarbonate and 179 μl of pyridine are added to a solution of 389 mg (2.00 mmol) of 7-amino-5-chloroquinolin-8-ol in 5 ml of THF, and the mixture is stirred at room temperature for 18 hours. 403 mg (2.00 mmol) of 4-nitrophenyl chloroformate are then added, and the mixture is stirred at room temperature for 1 hour.

2.1 b) 368 mg (2.00 mmol) of C-phenyl-C-pyridin-2-ylm-ethylamine is then added, and the mixture is stirred at room temperature for 5 days. The solvent is distilled off, the residue is taken up in dichloromethane and washed with 0.1N HCl and 0.1N NaOH. The organic phase is dried over sodium sulfate, evaporated, and the residue is chromatographed on a silica gel column:

Tert-butyl 5-chloro-7-[3-(phenylpyridin-2-ylmethyl)ure-ido]quinolin-8-yl carboxylate as brown highly viscous oil; ESI 505.

2.2 550 mg (0.523 mmol) of tert-butyl 5-chloro-7-[3-(phe-nylpyridin-2-ylmethyl)ureido]quinolin-8-yl carboxylate are dissolved in 10 ml of a 4N solution of hydrogen chloride in dioxane, and the mixture is stirred at room temperature for 18 hours. The solvent is distilled off, and the residue is chromatographed: 1-(5-chloro-8-hydroxyquinolin-7-yl)-3-(phe-nylpyridin-2-ylmethyl)urea dihydrochloride as brown crystals; ESI 405.

$^1$H-NMR ($d_6$-DMSO): δ=6.02 (d, J=6.5 Hz, 1H), 7.30 (t, J=7.3 Hz, 1H), 7.38 (t, J=7.5 Hz, 2H), 7.49 (d, J=7.5 Hz, 2H), 7.56 (m, 1H), 7.60 (dd, $J_1$=16 Hz, $J_2$=8.5 Hz, 1H), 7.81 (d, J=7.5 Hz, 1H), 8.12 (t, J=6.5 Hz, 1H), 8.44 (d, J=6.5 Hz, 1H), 8.47 (d, J=8.5 Hz, 1H), 8.63 (s, 1H), 8.68 (d, J=4.5 Hz, 1H), 8.92 (d, J=3 Hz, 1H), 9.08 (s, 1H), 10.6 (bs, 1H).

The following compounds are obtained analogously

| Compound No. | Structure/name |
|---|---|
| "A15" | 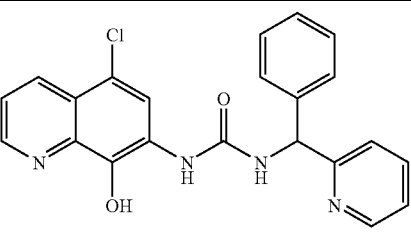<br>1-(5-Chloro-8-hydroxyquinolin-7-yl)-3-(phenyl-pyridin-2-ylmethyl)urea |

| Compound No. | Structure/name |
|---|---|
| "A16" | 1-(5-Chloro-8-hydroxyquinolin-7-yl)-3-((S)-1-cyclohexylethyl)urea |
| "A17" | 1-(5-Chloro-8-hydroxyquinolin-7-yl)-3-(2-ethoxyphenyl) urea |
| "A18" | 1-(8-Hydroxyquinolin-7-yl)-3-(1 2,3,4-tetrahydronaphthalen-1-yl)urea |
| "A19" | 1-(8-Hydroxyquinolin-7-yl)-3-(4-trifluoromethylphenyl)urea |
| "A20" | 1-(2-Ethoxyphenyl)-3-(8-hydroxyquinolin-7-yl)-urea |
| "A21" | 1-(5-Chloro-8-hydroxyquinolin-7-yl)-3-(4-trifluoromethylphenyl)urea |

| Compound No. | Structure/name |
|---|---|
| "A22" | 1-Benzyl-3-(5-chloro-8-hydroxyquinolin-7-yl)urea |

EXAMPLE 3

The preparation of 1-(2-hydroxyphenyl)-3-(8-hydroxyquinolin-7-yl)urea ("A24") is carried out analogously to the following scheme

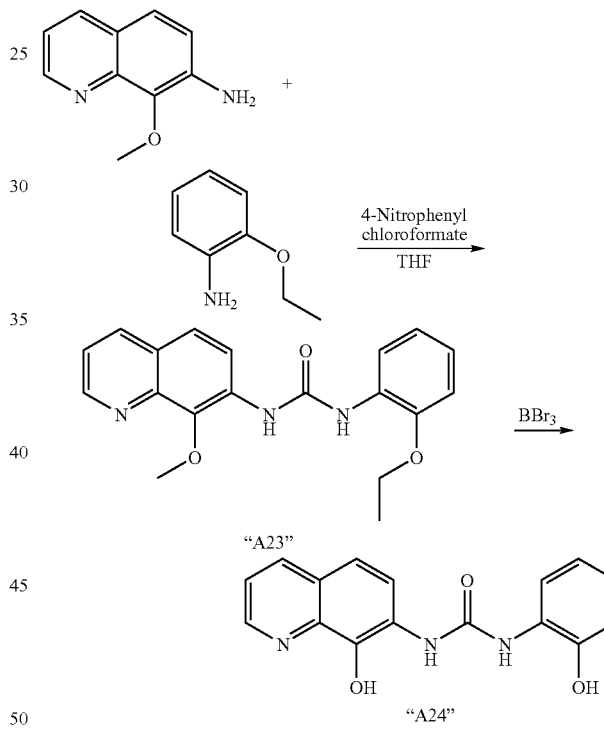

EXAMPLE 4

The preparation of 1-(2-trifluoromethylphenyl)-3-(8-hydroxyquinolin-7-yl)urea ("A26") is carried out analogously to the following scheme

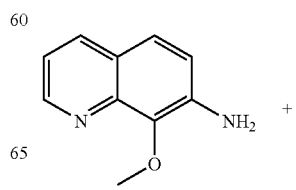

-continued

"A25"

4-Nitrophenyl chloroformate / THF

BBr₃

"A26"

TABLE 1

Inhibition of the proliferation of tumour cells IC₅₀ [mol/l]

| Compound No. | IC₅₀ |
|---|---|
| "A1" | 9.00E−08 |
| "A2" | 2.10E−06 |
| "A3" | 1.10E−06 |
| "A14" | 9.00E−08 |
| "A19" | 1.50E−06 |
| "A20" | 2.10E−07 |

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

I in which
$R^1$ denotes H,
$R^{1'}$ denotes H,
$R^2$ denotes H, OA or Hal,
$R^3$ denotes

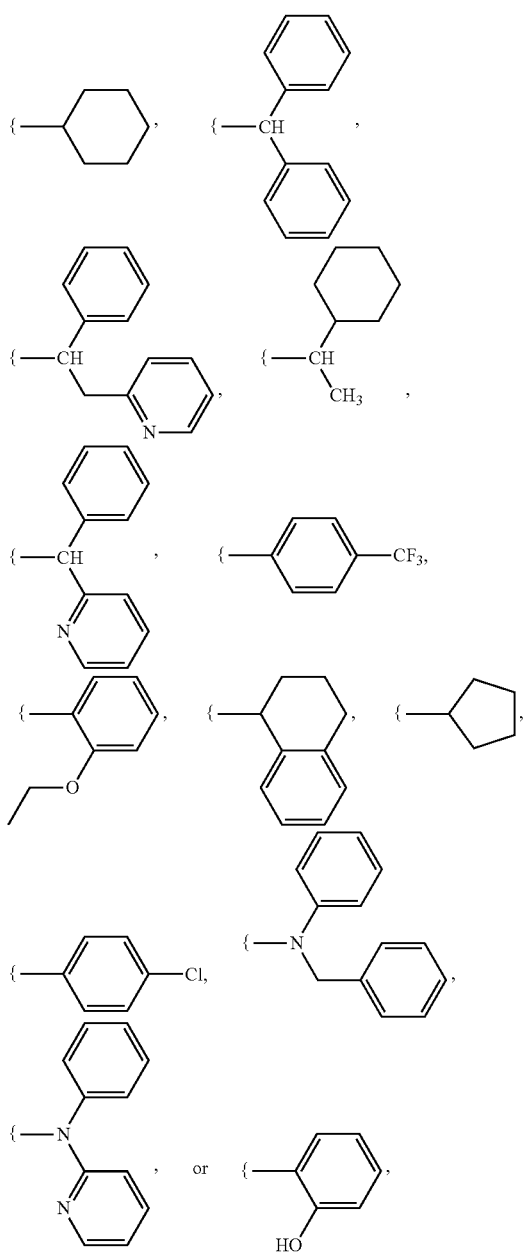

X is absent, or denotes CH₂ or NH,
Y is absent,
A is unbranched or branched alkyl having 1-10 C atoms, in which 1-7 H atoms are optionally replaced by F, Cl and/or Br, cycloalkyl having 3-8 C atoms, or cycloalkylalkylene having 4-10 C atoms, and
Hal denotes F, Cl, Br or I,
or a pharmaceutically usable salt, tautomer or stereoisomer thereof, including mixtures thereof in all ratios.

2. A compound according to claim 1, wherein
$R^1$, $R^{1'}$ denote H,
$R^2$ denotes H, OA or Hal,
X is absent, or denotes CH₂ or NH,
Y is absent,
A in each case, independently of one another, denotes unbranched or branched alkyl having 1-10 C atoms, in which 1-7 H atoms are optionally replaced by F, Cl and/or Br, cycloalkyl having 3-8 C atoms, or cycloalkylalkylene having 4-10 C atoms, and
Hal denotes F, Cl, Br or I,
or a pharmaceutically usable salt, tautomer or stereoisomer thereof, including mixtures thereof in all ratios.

3. A compound according to claim 1, wherein
$R^1$, $R^{1'}$ denote H,
$R^2$ denotes H, OA or Hal,
X is absent, or denotes CH₂ or NH,
Y is absent,
A in each case, independently of one another, denotes unbranched or branched alkyl having 1-10 C atoms, in which 1-7 H atoms are optionally replaced by F, Cl and/or Br, cycloalkyl having 3-8 C atoms or cycloalkylalkylene having 4-10 C atoms, and
Hal denotes F, Cl, Br or I,
or a pharmaceutically usable salt, tautomer or stereoisomer thereof, including mixtures thereof in all ratios.

4. A compound according to claim 1, wherein said compound is selected from the group:

| Compound No. | Structure/name |
|---|---|
| "A1" | 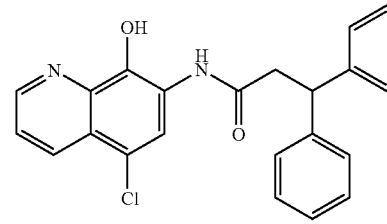<br>N-(5-chloro-8-hydroxyquinolin-7-yl)-3,3-diphenylpropionamide |
| "A2" | 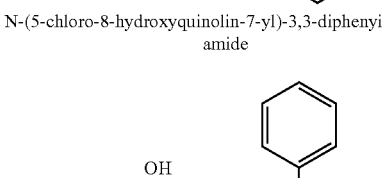<br>N-(5-chloro-8-hydroxyquinolin-7-yl)-2,2-diphenylacetamide |
| "A3" | 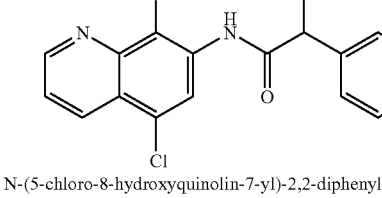<br>N-(5-chloro-8-hydroxyquinolin-7-yl)-2-phenyl-3-pyridin-2-ylpropionamide |

| Compound No. | Structure/name |
|---|---|
| "A4" | N-(5-chloro-8-hydroxyquinolin-7-yl)-2-(4-trifluoromethyl-phenyl)acetamide |
| "A5" | 2-Cyclopentyl-N-(8-hydroxyquinolin-7-yl)acetamide |
| "A6" | N-(8-hydroxyquinolin-7-yl)-2-(4-trifluoromethylphenyl)-acetamide |
| "A8" | N-(5-chloro-8-hydroxyquinolin-7-yl)-2-cyclopentyl-acetamide |
| "A9" | N-(5-chloro-8-hydroxyquinolin-7-yl)-2-(4-chlorophenyl)-acetamide |
| "A10" | 2-(Benzylphenylamino)-N-(5-chloro-8-hydroxyquinolin-7-yl)acetamide |
| "A12" | N-(8-hydroxyquinolin-7-yl)-3,3-diphenylpropionamide |
| "A13" | N-(5-chloro-8-hydroxyquinolin-7-yl)-2-(phenylpyridin-2-yl-amino)acetamide |
| "A14" | 1-(5-Chloro-8-hydroxyquinolin-7-yl)-3-(phenylpyridin-2-yl-methyl)urea |
| "A15" | 1-(5-Chloro-8-hydroxyquinolin-7-yl)-3-(phenylpyridin-2-yl-methyl)urea |
| "A17" | 1-(5-Chloro-8-hydroxyquinolin-7-yl)-3-(2-ethoxyphenyl)-urea |
| "A18" | 1-(8-Hydroxyquinolin-7-yl)-3-(1,2,3,4-tetrahydronaphthalen-1-yl)urea |

| Compound No. | Structure/name |
|---|---|
| "A19" | ![structure] 1-(8-Hydroxyquinolin-7-yl)-3-(4-trifluoromethylphenyl)urea |
| "A20" | ![structure] 1-(2-Ethoxyphenyl)-3-(8-hydroxyquinolin-7-yl)urea |
| "A21" | ![structure] 1-(5-Chloro-8-hydroxyquinolin-7-yl)-3-(4-trifluoromethyl-phenyl)urea |
| "A24" | ![structure] 1-(2-Hydroxyphenyl)-3-(8-hydroxyquinolin-7-yl)urea |
| "A26" | ![structure] 1-(2-Trifluoromethylphenyl)-3-(8-hydroxyquinolin-7-yl)urea | and pharmaceutically usable salts, tautomers and stereoisomers thereof, including mixtures thereof in all ratios.

5. A process for the preparation of compounds of according to claim 1, and pharmaceutically usable salts, tautomers and stereoisomers thereof, said process comprising:

a) for the preparation of compounds of the formula I in which X is absent or denotes $CH_2$, reacting a compound of formula II

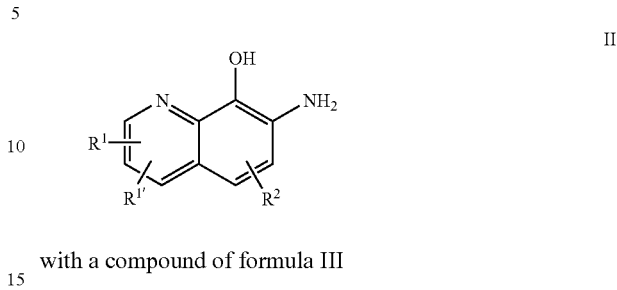

with a compound of formula III

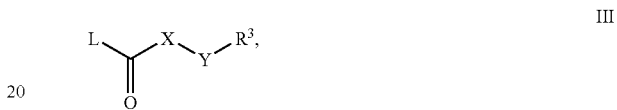

in which X is absent or denotes $CH_2$, and L denotes Cl, Br, I or a free or reactively functionally modified OH group, or b) for the preparation of compounds of the formula I in which X denotes $NR^6$,
reacting a compound of formula II with a compound of formula IV

or c) liberating a compound of formula I from one of its functional derivatives by treatment with a solvolyzing or hydrogenolyzing agent, or d) for the preparation of compounds of the formula I in which X denotes $NR^6$ or O,
reacting a compound of formula V

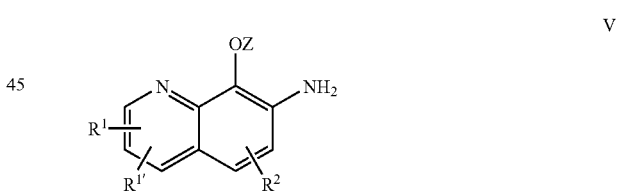

in which Z denotes a hydroxyl-protecting group,
with a coupling reagent selected from
a) isoproylidene chloroformate,
b) p-nitrophenyl chloroformate,
c) diphosgene, and
d) triphosgene,
and a compound of formula VI

in which X denotes $NR^6$ or O, and the hydroxyl-protecting group Z is subsequently cleaved off,
and/or e) converting a base or acid of formula I into one of its salts.

6. A pharmaceutical composition comprising at least one compound according to claim 1, and at least one excipient or adjuvant.

7. A compound according to claim 1, in which
  $R^1$, $R^{1'}$ denote H,
  $R^2$ denotes H, OA or Cl,
  X is absent, or denotes $CH_2$ or NH,
  Y is absent, and
  A in each case, independently of one another, denotes unbranched or branched alkyl having 1-5 C atoms, in which 1-3 H atoms are each optionally replaced by F, Cl and/or Br,
  cycloalkyl having 4-6 C atoms or cycloalkylalkylene having 4-6 C atoms.

8. A compound according to claim 1, in which
  $R^1$, $R^{1'}$ denote H,
  $R^2$ denotes H or Cl, and
  X is $CH_2$.

9. A compound according to claim 1, in which
  $R^1$, $R^{1'}$ denote H,
  $R^2$ denotes H or Cl, and
  X is NH.

10. A compound according to claim 1, wherein said compound is selected from:
  N-(5-chloro-8-hydroxyquinolin-7-yl)-3,3-diphenylpropionamide,
  N-(5-chloro-8-hydroxyquinolin-7-yl)-2,2-diphenylacetamide,
  N-(5-chloro-8-hydroxyquinolin-7-yl)-2-phenyl-3-pyridin-2-ylpropionamide,
  N-(5-chloro-8-hydroxyquinolin-7-yl)-2-(4-trifluoromethylphenyl)acetamide,
  2-Cyclopentyl-N-(8-hydroxyquinolin-7-yl)acetamide,
  N-(8-hydroxyquinolin-7-yl)-2-(4-trifluoromethylphenyl)acetamide,
  N-(5-chloro-8-hydroxyquinolin-7-yl)-3,3-dimethylbutyramide,
  N-(5-chloro-8-hydroxyquinolin-7-yl)-2-cyclopentylacetamide,
  N-(5-chloro-8-hydroxyquinolin-7-yl)-2-(4-chlorophenyl)acetamide, and
  2-(Benzylphenylamino)-N-(5-chloro-8-hydroxyquinolin-7-yl)acetamide,
    and pharmaceutically usable salts, tautomers and stereoisomers thereof, including mixtures thereof in all ratios.

11. A compound according to claim 1, wherein said compound is selected from:
  N-(8-hydroxyquinolin-7-yl)-3,3-diphenylpropionamide,
  N-(5-chloro-8-hydroxyquinolin-7-yl)-2-(phenylpyridin-2-ylamino)acetamide,
  1-(5-Chloro-8-hydroxyquinolin-7-yl)-3-(phenylpyridin-2-ylmethyl)urea,
  1-(5-Chloro-8-hydroxyquinolin-7-yl)-3-(phenylpyridin-2-ylmethyl)urea,
  1-(5-Chloro-8-hydroxyquinolin-7-yl)-3-((S)-1-cyclohexylethyl)urea,
  1-(5-Chloro-8-hydroxyquinolin-7-yl)-3-(2-ethoxyphenyl)urea, and
  1-(8-Hydroxyquinolin-7-yl)-3-(1,2,3,4-tetrahydronaphthalen-1-yl)urea,
    and pharmaceutically usable salts, tautomers and stereoisomers thereof, including mixtures thereof in all ratios.

12. A compound according to claim 1, wherein said compound is selected from:
  1-(8-Hydroxyquinolin-7-yl)-3-(4-trifluoromethylphenyl)urea,
  1-(2-Ethoxyphenyl)-3-(8-hydroxyquinolin-7-yl)urea,
  1-(5-Chloro-8-hydroxyquinolin-7-yl)-3-(4-trifluoromethylphenyl)urea,
  1-Benzyl-3-(5-chloro-8-hydroxyquinolin-7-yl)urea,
  1-(2-Hydroxyphenyl)-3-(8-hydroxyquinolin-7-yl)urea, and
  1-(2-Trifluoromethylphenyl)-3-(8-hydroxyquinolin-7-yl)urea,
    and pharmaceutically usable salts, tautomers and stereoisomers thereof, including mixtures thereof in all ratios.

13. A compound selected from the group:

| Compound No. | Structure/name |
|---|---|
| "A7" | 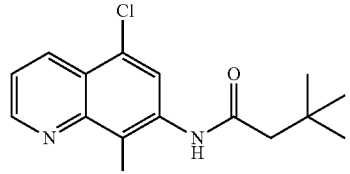<br>N-(5-chloro-8-hydroxyquinolin-7-yl)-3,3-dimethyl-butyramide |
| "A16" | 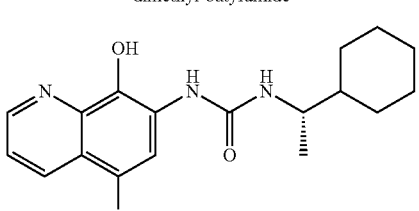<br>1-(5-Chloro-8-hydroxyquinolin-7-yl)-3-((S)-1-cyclohexylethyl)urea |
| "A22" | 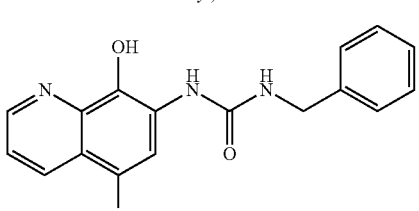<br>1-Benzyl-3-(5-chloro-8-hydroxyquinolin-7-yl)urea | and pharmaceutically usable salts, tautomers and stereoisomers thereof, including mixtures thereof in all ratios.

14. A compound according to claim 4, wherein said compound is N-(5-chloro-8-hydroxyquinolin-7-yl)-3,3-diphenylpropionamide or a pharmaceutically usable salt, tautomer or stereoisomer thereof, including mixtures thereof in all ratios.

15. A compound according to claim 4, wherein said compound is N-(5-chloro-8-hydroxyquinolin-7-yl)-2,2-diphenylacetamide or a pharmaceutically usable salt, tautomer or stereoisomer thereof, including mixtures thereof in all ratios.

16. A compound according to claim 4, wherein said compound is N-(5-chloro-8-hydroxyquinolin-7-yl)-2-phenyl-3-pyridin-2-ylpropionamide or a pharmaceutically usable salt, tautomer or stereoisomer thereof, including mixtures thereof in all ratios.

* * * * *

UNITED STATES PATENT AND TRADEMARK OFFICE
CERTIFICATE OF CORRECTION

PATENT NO. : 8,158,799 B2
APPLICATION NO. : 12/097153
DATED : April 17, 2012
INVENTOR(S) : Oliver Schadt et al.

It is certified that error appears in the above-identified patent and that said Letters Patent is hereby corrected as shown below:

Title page, (73) Assignee Line 2 reads: "Meschraenkter Haftung" should read --Beschraenkter Haftung--.

Signed and Sealed this
Nineteenth Day of June, 2012

David J. Kappos
*Director of the United States Patent and Trademark Office*